United States Patent [19]
Balestracci

[11] Patent Number: 5,997,514
[45] Date of Patent: Dec. 7, 1999

[54] FINGER GRIP COLLAR FOR A SYRINGE OR CARTRIDGE BARREL

[75] Inventor: Ernest Balestracci, Iseline, N.J.

[73] Assignee: Brocco Research, USA, Princeton, N.J.

[21] Appl. No.: 09/232,037

[22] Filed: Jan. 15, 1999

[51] Int. Cl.[6] .................................................. A61M 5/00
[52] U.S. Cl. .......................................... 604/227; 604/187
[58] Field of Search .................................. 604/227, 220, 604/187, 232

[56] References Cited

U.S. PATENT DOCUMENTS

| | | | |
|---|---|---|---|
| 3,978,858 | 9/1976 | Tischlinger | 128/237 |
| 5,115,816 | 5/1992 | Lee | 528/749 |
| 5,554,133 | 9/1996 | Haffner et al. | 604/227 |
| 5,573,514 | 11/1996 | Stiehl et al. | 604/198 |
| 5,607,399 | 3/1997 | Grimard et al. | 604/220 |
| 5,697,918 | 12/1997 | Flasher et al. | 604/227 |

FOREIGN PATENT DOCUMENTS

WO 97/11728  3/1997  WIPO.

*Primary Examiner*—John D. Yasko
*Attorney, Agent, or Firm*—Imre Balogh

[57] ABSTRACT

Finger grip collar positioned on the proximal end of a syringe or cartridge barrel by a snap-on motion to facilitate manipulation of the syringe or cartridge during the injection or withdrawal of a medical fluid into or from a site. The finger grip collar requires no special orientation or positioning on the barrel of the syringe or cartridge for the practitioner to manipulate the assemblage.

4 Claims, 4 Drawing Sheets

FINGER GRIP COLLAR FOR A SYRINGE OR CARTRIDGE BARREL

BACKGROUND OF THE INVENTION

1. Field of the Invention

This invention relates to a finger grip collar designed to be placed on the proximal end of a syringe or cartridge barrel to facilitate the use of the same during the injection process.

2. Reported Developments

Syringes and cartridges made of glass or polymeric material for delivery of fluids to and from a patient have been proposed and utilized by the prior art, and have achieved a highly developed state. Various requirements related to specific delivery systems have also been addressed. While specific requirements of fluid delivery to and from a patient may vary, means of delivery remain essentially the same and may be characterized by the following general description of a syringe.

A syringe comprises:

a) a cylindrical barrel having a proximal end designed for receiving a plunger, with or without a plunger rod removably attached to the plunger or being integral with the plunger, and a distal end adapted to mount a needle or luer connector thereon; and b) a plunger slidably mounted in the barrel.

The plunger is inserted into the barrel at the proximal end of the syringe and thus, when fluid is contained in the barrel it may be expelled by pushing the plunger in the barrel towards its distal end; or when the syringe is used to withdraw fluid from a patient, the plunger located at the distal end of the barrel is pulled towards the proximal end of the syringe thereby drawing fluid into the barrel. Since a fluid-tight seal is necessary between the plunger and the inside wall of the barrel, a resilient rubber tip is positioned on the distal end of the plunger, or typically, the plunger is made of resilient rubber-like material. In some of the syringes of the prior art the rubber tip has been replaced with a generally flat, circular disk.

In order to assure air-tight seal between the inside wall of the syringe barrel and the plunger, prior art plungers are manufactured with a larger outside diameter than the inside diameter of the syringe barrels. When the plunger is introduced into the syringe barrel, it is sufficiently compressed to provide adequate pressure between the inside wall of the syringe and the plunger to seal the interface and withstand the challenges of filling, injecting and withdrawing fluids using the syringe without leakage.

In both the rubber and thermoplastic plungers a relatively large compressive force must be exerted on the plungers by the syringe barrel to provide for a tight, leak-proof seal. This quality of the seal, however, makes the movement of the plunger difficult. To remedy the problem the prior art used lubricants to reduce friction and drag between the plunger and the inside surface of the syringe barrel. The use of such lubricants, however, is also undesirable with certain parenteral fluids which tend to disperse or dissolve in the parenteral fluids thereby contaminating the parenteral fluids. Attempts to avoid the use of lubricants included the use of various plunger configurations, such as plungers that were provided with one or more ribs projecting fowardly or rearwardly in the barrel to reduce the frictional drag between the plunger and the inside surface of the barrel.

In using the syringe for injection to the patient or withdrawing fluid from the patient, the practitioner encounters two kinds of forces:

breakaway forces and running forces. The former relate to the forces at the start of the injection or withdrawal process necessary to move the plunger from its stationary position and the latter relates to the forces necessary to maintain the movement of the plunger at a steady rate of speed. Typically, the practitioner uses three fingers on one hand during the injection process to overcome/exert these forces: the thumb which exerts a force on the plunger rod and the index and middle fingers which hold the barrel of the syringe.

Recognizing the need to overcome the breakaway and running forces in a syringe, the prior art provided finger rests or finger-grip flanges on syringe barrels so that the practitioner could more securely and safely hold syringe barrel. Illustrative examples are U.S. Pat. Nos. 3,978,858; 5,115,816; 5,554,133; 5,573,514; 5,607,399; 5,697,918; and WO 97/11728.

It has been observed by practitioners that syringes equipped with finger rests or finger-grip flanges help in overcoming the breakaway and running forces during injections, however, practitioners would prefer to have a greater gripping surface so that control and accuracy of the amount of the fluid media delivered to the patient from the syringe would be more reliable.

It has also been observed that syringes equipped with finger rests or finger-grip flanges require specific orientation during the injection, i.e., the index and middle fingers should grip the finger rests or finger-grip flanges in order to achieve a secure holding of the syringe by the practitioner. This specific orientation is often missed especially under emergency situations.

With respect to glass syringes which typically are equipped with integral flanges of small gripping surface, the danger of breakage at the finger-grip flange exists during the injection process. Such breaking of the glass flange have been known to cause serious finger injuries to the practitioner. This hazard of injury is even more accentuated in the case of the so-called "flangeless" syringes where the proximal end of the barrel is constituted by a relatively narrow rim integral with the barrel.

I have now discovered that the above-mentioned shortcomings in syringes and cartridges may be overcome by an inexpensive snap-on finger-grip collar designed to accommodate various size barrels with or without integral finger rest or finger-grip flanges.

SUMMARY OF THE INVENTION

In accordance with the present invention a finger grip collar is provided for the barrel of a cartridge or a syringe to be positioned by a snap-on motion onto the proximal end of the barrel of the syringe or the cartridge adjacent to the integral flange or rim of the barrel. The snap-on finger grip collar is applicable to both plastic and glass barrels and is designed to the dimensions of various barrels having a volume capacity of from 5 to 500 mls or more.

The finger grip collar is of generally oval or elliptical shape configuration on the outside, finger contacting side thereof allowing comfortable gripping contact between the finger grip collar and the index and middle fingers of the practitioner. The inside of the finger grip collar which faces the barrel is of circular/cylindrical configuration to conform to the circular/cylindrical shape of the barrel. The finger grip collar has a gap through which the barrel is snapped into the circular inside thereof. The diameter of the circular inside of the finger grip collar is essentially the same as the outside diameter of the barrel, while the gap is somewhat smaller than the outside diameter of the barrel so that after positioning the finger grip collar on the barrel, the barrel will be locked in place. This snap-on provision is enabled by the material of construction which material is a hard, but somewhat flexible plastic material which flexes sufficiently under manual pressure of the user. In accordance, the finger grip collar is fabricated of known plastic materials using known precision molding techniques. Suitable plastics include polypropylene, polystyrene, polycarbonates, nylon, acetates, polyethylene and polyesters. These plastic materials can include lubricant to facilitate the snapping motion of the finger grip collar onto the barrel. A preferred slip agent is PETRAC SLIP-EZE OLEAMIDE, a fatty amide commercially available from Synpro, Cleveland, Ohio.

DETAILED DESCRIPTION OF THE INVENTION

Figure 1:
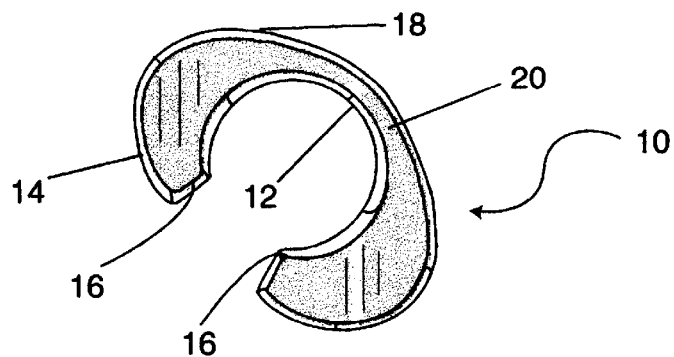
FIG. 1 is a perspective view of the finger grip collar of the present invention.
Figure 2:
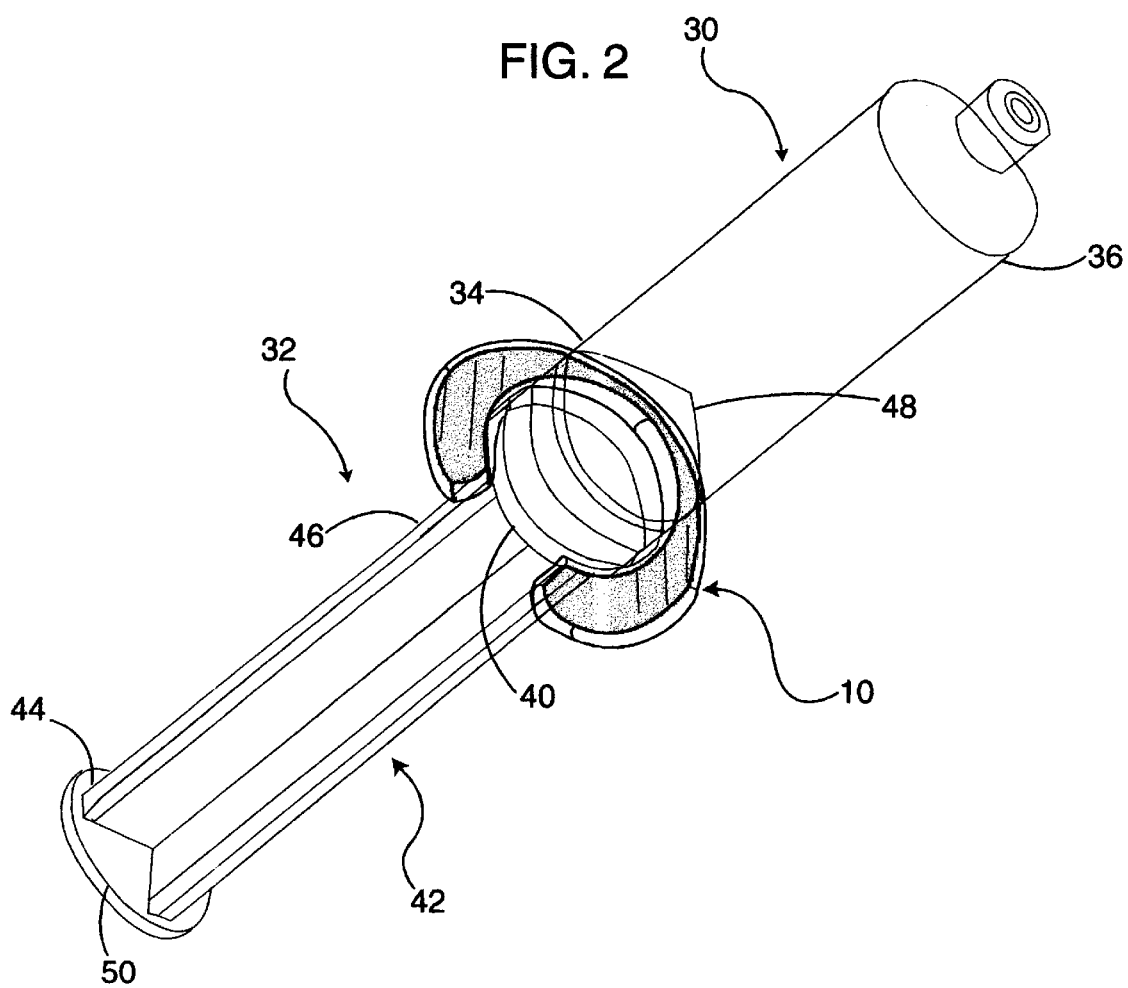
FIG. 2 is a perspective view of the finger grip collar shown in FIG. 1 placed on the barrel of a cartridge.
Figure 3:
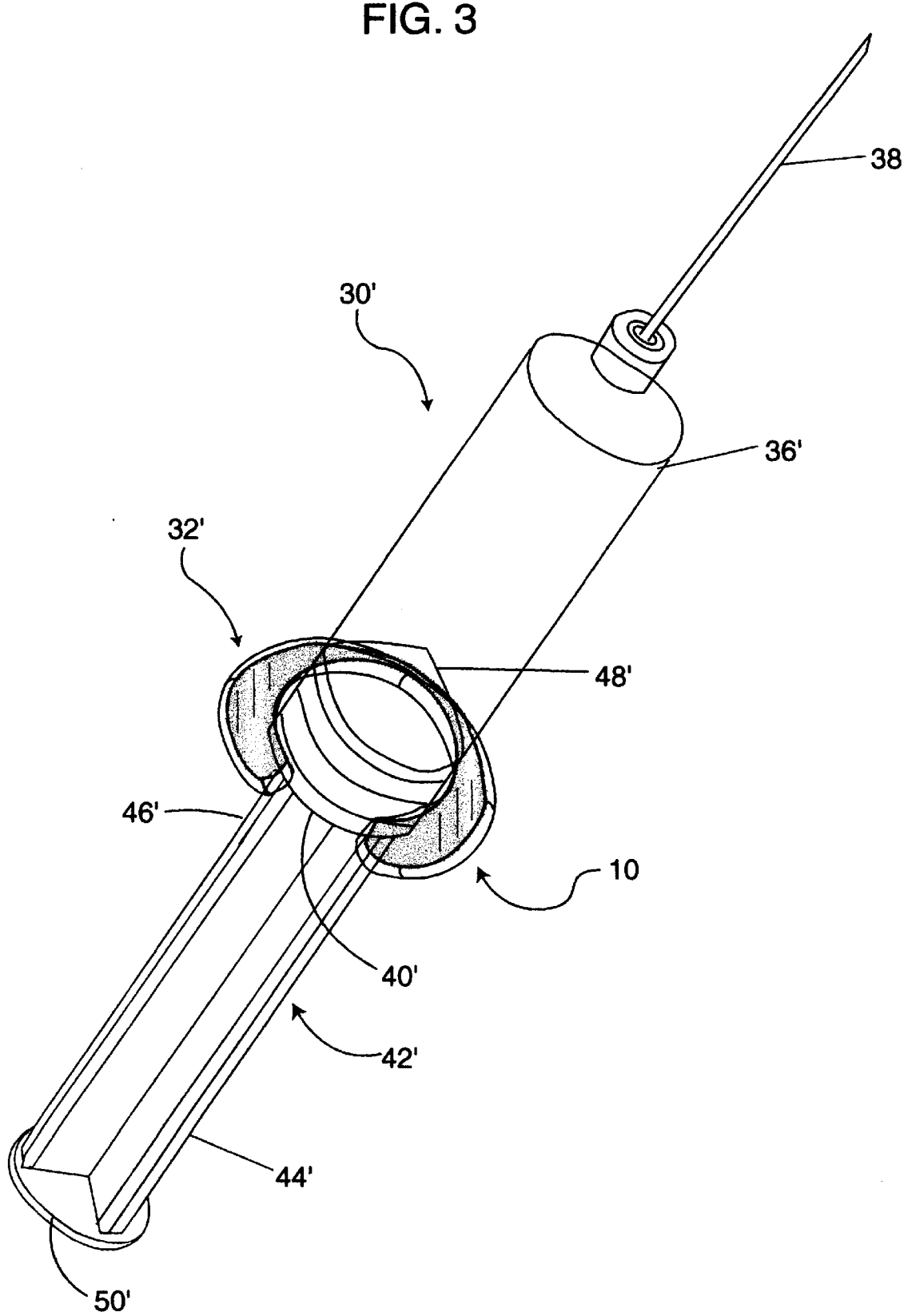
FIG. 3 is a perspective view of the finger grip collar shown in FIG. 1 placed on the barrel of a syringe.

Referring to the drawings wherein like numerals with primes (') represent like components, FIG. 1 shows a perspective view of the finger grip collar 10 of the present invention which is placed on the barrel 30 of cartridge 32, shown in FIG. 2, or on the barrel 30' of syringe 32' shown in FIG. 3. The cartridge or the syringe can be empty or can be pre-filled with a medical fluid. The finger grip collar may be placed on the barrel at the manufacturing site or packaged separately and placed on the barrel by a snap-on motion just prior to using the cartridge or syringe for administration, or withdrawal of a medical fluid. The finger grip collar is preferably used on pre-filled cartridge-needle units which are in widespread commercial use. Some of these pre-filled cartridge-needle units comprise a barrel with an integral flange on the proximal ends thereof, while the barrels of other cartridge-needle units include only a small integral rim on the proximal ends thereof. The present invention is utilizable on both types of cartridge-needle units.

FIG. 2 shows a typical empty cartridge to which a needle can be attached as shown in FIG. 3 or, alternatively, an other access means such as a luer connector can replace the needle. The typical cartridge 32 or 32' comprises:

a) a cylindrical barrel 30 or 30' having a proximal end 34 or 34' for receiving a plunger and a distal end 36 or 36' for mounting an access means thereon, such as a luer connector or a needle 38, said distal end being equipped with an integral flange or rim 40 or 40';

b) a plunger rod 42 or 42' having a proximal end 44 or 44' and a distal end 46 or 46';

c) a plunger 48 or 48' removably attached or being integral with the plunger rod at the distal end thereof; and d) a thumb rest 50 or 50' at the proximal end 44 or 44' of plunger rod 42 or 42'.

Finger grip collar 10 is positioned on the proximal end of cylindrical barrel 34 or 34' adjacent to integral flange or rim 40 or 40' by a snap-on motion.

Figure 4:
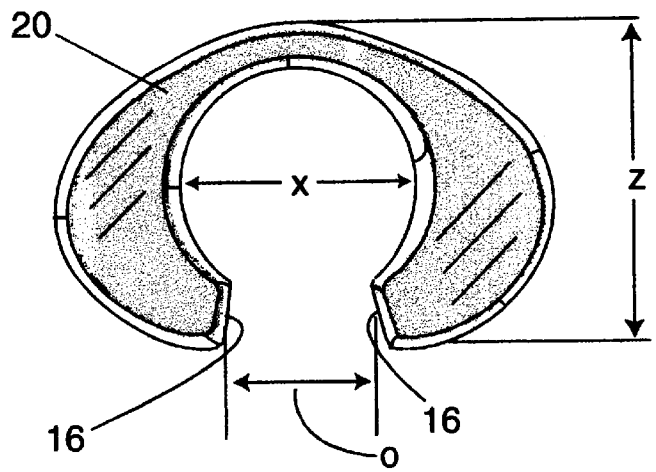
FIG. 4 is a top plan view of the finger grip collar shown in FIG. 1, the bottom plan view thereof being identical to the top plan view thereof.

Finger grip collar 10 as shown in top plan view in FIG. 4 is of a generally oval or elliptical configuration on the outside thereof to accommodate the fingers of the user, and it is of circular configuration on the inside thereof to accommodate barrel 30 or 30' and to hold the barrel in a secure position during injection or withdrawal of a medical fluid.

The finger grip collar is sized to receive barrels having various outside diameters. As readily appreciated by the skilled artisan, barrels having a volume capacity of 20 to 100 ml or more require the inside of the finger grip collar to approximately match the circumferential size of the cylindrical barrel.

FIG. 1 shows a perspective view and FIG. 4 shows a top plan view of the finger grip collar 10 having an inside wall 12 of circular configuration and an outside wall 14 of a generally oval or elliptical configuration. A gap or opening O defined by the transition points 16 where the inside and outside walls meet are designed to receive a barrel therethrough and into the circularly configured inside of the finger grip collar. The inside and outside walls may be rimmed, the rim 18 slightly rising vertically above and below the horizontal plane surface 20 of the finger grip collar. Typically, the height of the rim is about 2 to 5 mm.

Figure 5:
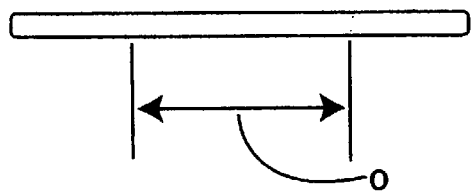
FIG. 5 is a front elevational view of the finger grip collar of FIG. 1.
Figure 6:
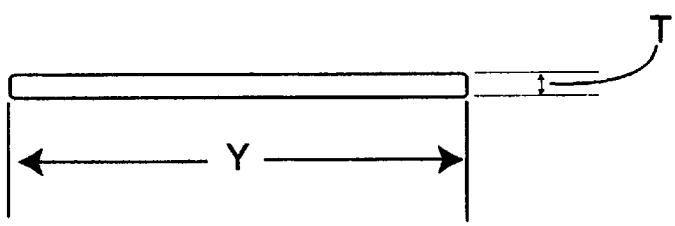
FIG. 6 is a rear elevational view of the finger grip collar of FIG. 1.
Figure 7:
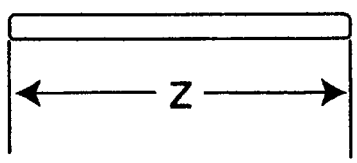
FIG. 7 is a right-side elevational view of the finger grip collar of FIG. 1, the left side elevational view thereof being identical with the right-side elevational view thereof.

FIG. 5 is a front elevational view, FIG. 6 is a rear elevational view and FIG. 7 is a right-side elevational view of the finger grip collar, the left-side elevational view being identical with the right-side elevational view thereof. Referring to a representative embodiment of the finger grip collar of the present invention shown in FIGS. 4–7, the finger grip collar which accommodates the barrel of a cartridge or a syringe having a diameter of about 25 mm, the approximate dimensions are as follows:

The diameter of X of the circle enclosed by the inside wall of the finger grip collar is about 20 to 30 mm as shown in FIG. 4;

The diameter Y of the flat body enclosed by the outside wall of the finger grip collar is about 50 to 60 mm as shown in FIG. 6;

The diameter Z of the finger grip collar is about 25 to 30 mm as shown in FIG. 7;

The diameter O of the gap or opening into the circular inside defined by the inside wall of the finger grip collar is about 20 to 25 mm as shown in FIGS. 4 and 5; and The thickness T of the finger grip collar is about 2 to 10 mm.

Figure 8:
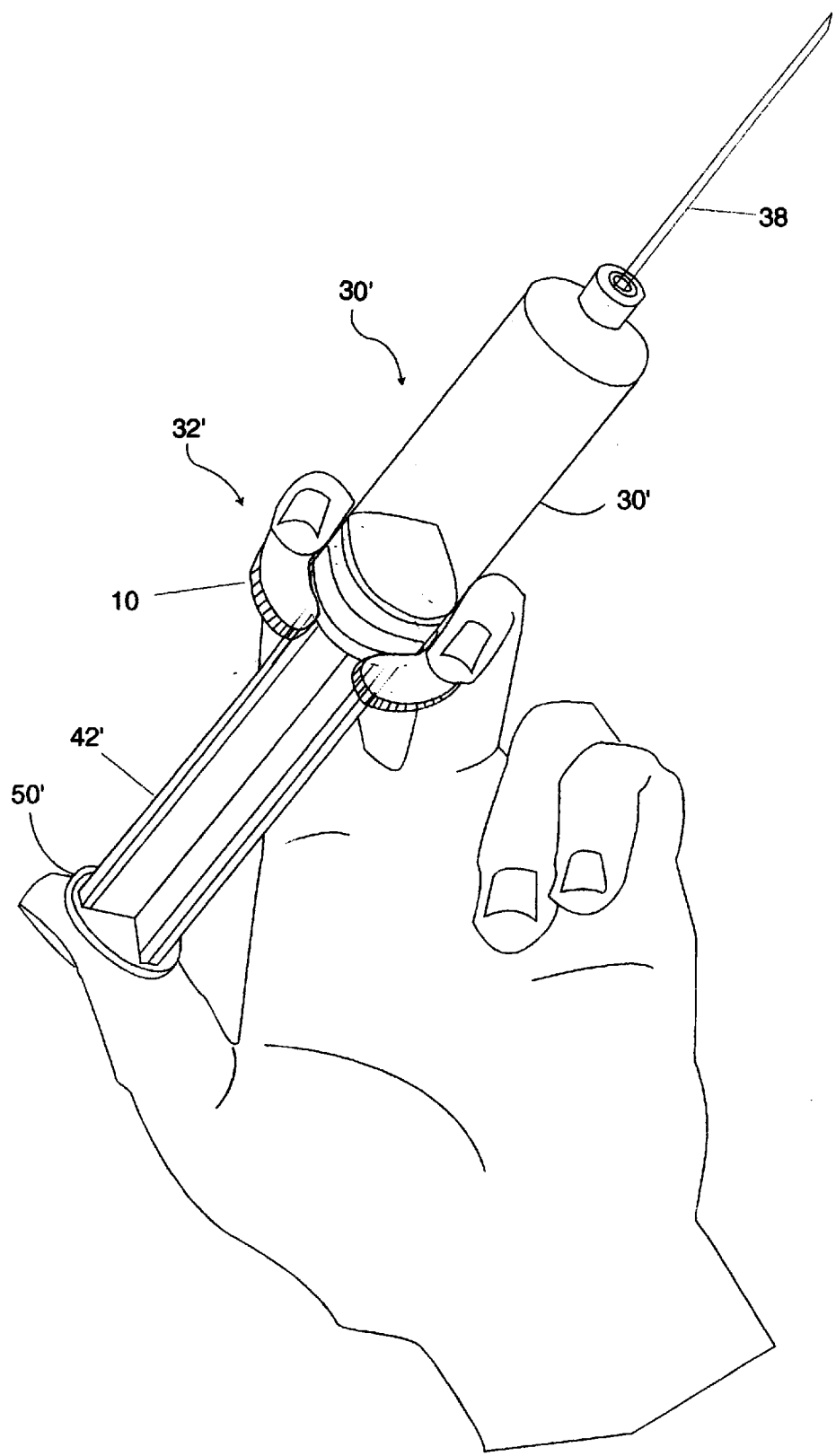
FIG. 8 shows in perspective view the finger grip collar shown in FIG. 3 placed on the barrel of a syringe operated by one hand of a practitioner.

FIG. 8 illustrates in a perspective view the finger grip collar placed on the barrel of a syringe and the combination being operated by one hand of a practitioner. The index and middle fingers are placed on the finger grip collar 10, the barrel 30' being positioned between the fingers, and the thumb is placed on the thumb rest 50' of plunger rod 42'. Manual force is exerted on the thumb rest by the thumb and on finger grip collar by the index and middle fingers of the practitioner resulting in the sliding movement of plunger 48' in barrel 30' resulting in expulsion of the medical fluid contained in the barrel through needle 38.

| REFERENCE NUMERALS AND LETTERS USED IN THE SPECIFICATION | |
| --- | --- |
| Finger grip collar | 10 |
| Cylindrical barrel | 30, 30' |
| Cartridge with plunger and plunger rod, generally designated | 32, 32' |
| Proximal end of cylindrical barrel | 34, 34' |
| Distal end of cylindrical barrel | 36, 36' |
| Needle | 38 |
| Integral flange or rim on cylindrical barrel | 40, 40' |
| Plunger rod | 42 42' |
| Proximal end of plunger rod | 44, 44' |
| Distal end of plunger rod | 46, 46' |
| Plunger | 48, 48' |
| Thumb rest on plunger rod | 50, 50' |
| The diameter of the circular inside of the finger grip collar | X |
| The diameter of the outside wall of the finger grip collar | Y |
| The small outside diameter of the finger grip collar | Z |
| The thickness of the finger grip collar | T |
| Gap or opening into the circular inside of the finger grip collar | O |
| Inside wall of finger grip collar | 12 |
| Outside wall of finger grip collar | 14 |
| Transition points | 16 |
| Rim on the finger grip collar | 18 |
| The horizontal surface of the finger grip collar | 20 |

Having described the invention with specificities, these should not be construed as limitation on the scope thereof, but rather as exemptlifications of one preferred embodiment thereof.

What is claimed is:

1. A finger grip collar in combination with a syringe or cartridge to facilitate the use of said syringe or cartridge during the injection or withdrawal of a medical fluid into or from a site, said combination comprising:
   a) a cylindrical barrel having:
      an inside diameter;
      an outside diameter;
      an open proximal end for receiving a plunger, said open proximal end terminating in a rim or flange having a distal surface and a proximal surface; and a distal end for mounting a medical fluid access means thereon;
   b) a plunger, having an outside diameter equal to or slightly greater than the inside diameter of said cylindrical barrel, slideably positioned in said cylindrical barrel;
   c) a plunger rod having a proximal end and a distal end; said plunger rod being removably attached or being integral at its distal end with said plunger;
   d) a thumb rest at the proximal end of said plunger rod for facilitating exertion of manual pressure on said plunger rod;
   e) a finger grip collar being positioned on the open proximal end of said cylindrical barrel adjacent to said distal surface of said rim or flange, said finger grip collar consisting of:
      a flat resilient plastic body having a thickness of from about 2 to about 10 mm, said resilient plastic body having an elliptical outside wall, and a circular inside wall defining a cylindrical space within, wherein said cylindrical space has a diameter equal to or slightly greater than the outside diameter of said cylindrical barrel, said elliptical outside wall and said circular inside wall meeting at two points, said points being spaced from each other defining an opening into said cylindrical space, wherein said opening is slightly less or equal to the cylindrical space defined by said inside wall, wherein said resilient plastic body is of a material selected from the group consisting of polypropylene, polystyrene, polycarbonates, nylon, acetates, polyethylene and polyesters.

2. The finger grip collar in combination with a syringe or cartridge of claim 1 wherein said inside and outside walls terminate in a reinforcing integral rim extending upward and downward from the flat resilient plastic body of the finger grip collar.

3. The finger grip collar in combination with a syringe or cartridge of claim 2 wherein said reinforcing integral rim extending about 2 to 5 mm upward or downward from said resilient plastic body of the finger grip collar.

4. A process of assembling a finger grip collar and a syringe or cartridge, wherein said syringe or cartridge is pre-filled with a medical fluid, and delivering said medical fluid to a site by injection, comprising the steps of:
   (1) providing a syringe or cartridge comprising:
      a) a cylindrical barrel having:
         an inside diameter;
         an outside diameter;
         an open proximal end for receiving a plunger, said open proximal end terminating in a rim or flange having a distal surface and a proximal surface; and a distal end for mounting a medical fluid access means thereon;
      b) a plunger, having an outside diameter equal to or slightly greater than the inside diameter of said cylindrical barrel, slideably positioned in said cylindrical barrel;
      c) a plunger rod having a proximal end and a distal end; said plunger rod being removably attached or being integral at its distal end with said plunger;
      d) a thumb rest at the proximal end of said plunger rod for facilitating exertion of manual pressure on said plunger rod;
   (2) providing a finger grip collar consisting of:
      a flat resilient plastic body having a thickness of from about 2 to about 10 mm, said resilient plastic body having an elliptical outside wall, and a circular inside wall defining a cylindrical space within, wherein said cylindrical space has a diameter equal to or slightly greater than the outside diameter of said cylindrical barrel, said elliptical outside wall and said circular inside wall meeting at two points, said points being spaced from each other defining an opening into said cylindrical space, wherein said opening is slightly less or equal to the cylindrical space defined by said inside wall, wherein said resilient plastic body is of a material selected from the group consisting of polypropylene, polystyrene, polycarbonates, nylon, acetates, polyethylene and polyesters;
   (3) placing said finger grip collar on the proximal end of said barrel adjacent to said distal surface of said rim or flange by a snap-on motion;
   (4) engaging the finger grip collar with the index and middle fingers, and engaging the thumb rest on the proximal end of the plunger rod with the thumb finger by a practitioner; and
   (5) exerting manual force onto said finger grip collar and onto said thumb rest to expel said medical fluid from said syringe or cartridge.

\* \* \* \* \*